United States Patent
Wei et al.

[11] 3,935,202
[45] Jan. 27, 1976

[54] 3-(4-BIPHENYLYLCARBONYL)PROPIONAMIDO CEPHALOSPORIN DERIVATIVES

[75] Inventors: Peter H. L. Wei, Springfield; Ronald J. McCaully, Malvern, both of Pa.

[73] Assignee: American Home Products Corporation, New York, N.Y.

[22] Filed: Mar. 18, 1974

[21] Appl. No.: 452,017

[52] U.S. Cl............. 260/243 C; 424/246; 424/271; 260/239.1
[51] Int. Cl.[2]............... C07D 499/44; C07D 501/20
[58] Field of Search ................................ 260/243 C

[56] References Cited
UNITED STATES PATENTS
3,849,408  11/1974  Dolfini ........................... 260/243 C

*Primary Examiner*—Nicholas S. Rizzo
*Attorney, Agent, or Firm*—Richard K. Jackson

[57] ABSTRACT

The antibacterial agents of this invention present the following structural formula:

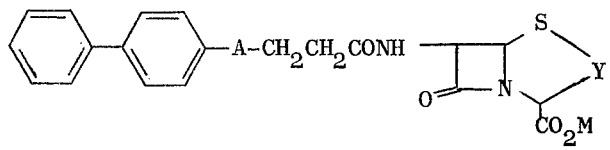

in which

A is a member selected from the group consisting of

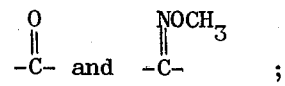

M is a member selected from the group consisting of —H, an alkali metal and —NH$_4$; and
Y is a member selected from the group consisting of

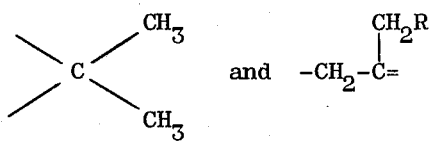

wherein
R is —H, alkanoyloxy of 2 to 6 carbon atoms,

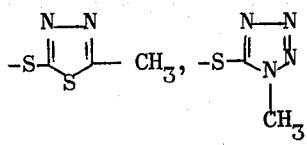

or, when taken with the 3-carboxy group,

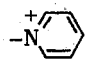

3 Claims, No Drawings

3-(4-BIPHENYLYLCARBONYL)PROPIONAMIDO CEPHALOSPORIN DERIVATIVES

DESCRIPTION OF THE INVENTION

In accordance with this invention there is provided antibacterial agents of the formula:

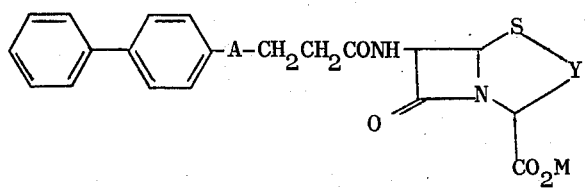

in which

A is a member selected from the group consisting of

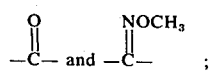

M is a member selected from the group consisting of —H, an alkali metal and —$NH_4$; and Y is a member selected from the group consisting of

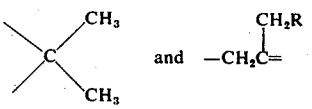

R is -H, alkanoyloxy of 2 to 6 carbon atoms,

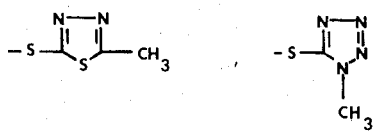

or, when taken with the 3-carboxy group,

The compounds of this invention are prepared by coupling techniques well known to the chemical arts. Thus, dehydrative coupling or mixed anhydride coupling as applied in the area of peptide synthesis are especially useful methods for the coupling reactions involved in the formation of the amides of 7-aminocephalosporanic acid derivatives and 6-amino penicillanic acid derivatives. In addition, the carboxylic acid intial reactants may, if desired, be converted to the corresponding acid halide by conventional means for use as the desired acylating agent.

The preferred cephalosporin derivatives from the standpoint of availability of reactants, ease of reaction and production economics are 7-amino-cephalosporanic acid and its desacetoxy analogue. However, those cephalosporin derivatives containing the

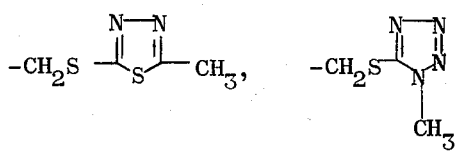

or 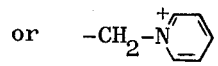

groups are recognized antibacterially equivalent derivations of the cephalosporanic acid moiety, as are the alkali metal and ammonium salts of the 3-carboxylic acid group.

3(4-Biphenylylcarbonyl)propionic acid is a known compound. The 3-(4-biphenylylcarbonyl)propionic acid O-methyloxime is prepared by refluxing equimolar amounts of 3-(4-biphenylylcarbonyl)propionic acid dissolved in dimethoxyethane and methoxyamine hydrochloride dissolved in an aqueous solution containing a molar equivalent of sodium acetate.

The compounds of this invention have been found to be active antibacterials effective against gram-positive and gram-negative test organisms as well as penicillin resistant staphlococcus, by using the well known and scientifically accepted agar serial dilution testing technique. Thus, the compounds of this invention are useful in the fields of comparative pharmacology and in microbiology and may be used for the treatment of bacterial infections amenable to treatment with penicillin and cephalosporin antibiotics.

The following examples illustrate the preparation of representative pencillin and cephalosporin derivatives. The activity of each product of the examples is presented for those specific bacterial strains against which the compound exemplified was active at or below 250 micrograms per milliliter. The representative nature of the bacterial strains employed to demonstrate antibacterial activity are indicative of the broader applicability of the compounds of this invention in the control of bacterial infestations other than those specifically referred to in each of the following examples. The bacterium are named followed by the specific strain and the concentration in micrograms per milliliter at which 100 percent inhibition occurred. The abbreviations for each bacterium are:

| | | |
|---|---|---|
| BA | SU | Bacillus subtilis |
| HE | SP | Herellea species |
| KL | PN | Klebsiella pneumoniae |
| NE | CA | Neisseria catarrhalis |
| PR | VU | Proteus vulgaris |
| ST | AU | Staphylococcus aureus |

EXAMPLE I

7-[3-(4-Biphenylylcarbonyl)propionamido]cephalosporanic acid.

To a tetrahydrofuran solution of 1.27 grams (5 millimole) of 3-(4-biphenylylcarbonyl)propionic acid in a salt-ice bath is added successively 0.50 gram of triethylamine and 0.70 gram (5 millimoles) of isobutyl chloroformate. After the solution is stirred for 15 minutes a cold solution of 1.36 grams (5 millimoles) of 7-aminocephalosporanic acid in a mixture of 20 milliliters tetrahydrofuran 0.5 g. of triethylamme and 10 milliliters $H_2O$ is added. The mixture is stirred in the ice-bath for 1 hour and at room temperature for 1 hour. After some solid is filtered off, the filtrate is evaporated under reduced pressure at approximately 30°C. The residue is dissolved in 50 milliliters $H_2O$ and some gelatinous solid is filtered off. The aqueous solution is acidified with a 6 N HCl solution to pH 2 in an ice-bath. The solid is collected and washed well with $H_2O$ and then dissolved in ethyl acetate. The ethyl acetate solution is dried over anhydrous $MgSo_4$. The residue that results after removal of the solvent is treated with diethyl ether and collected. The product (1.3 grams) is obtained as a polymorphous solid.

Elemental Analysis for $C_{26}H_{24}N_2O_7S\cdot\frac{1}{2}H_2O$: Calc'd: C, 60.33; H, 4.87; N, 5.41. Found: C, 60.77; H, 4.99; N, 5.25.

| BA | SU |  | 6633 | .488 |
| KL | PN |  | 10031 | 31.3 |
| NE | CA |  | 8193 | 31.3 |
| ST | AU |  | 6538P | .244 |
| ST | AU |  | SMITH | .244 |
| ST | AU |  | CHP | 1.95 |
| ST | AU |  | 53-180 | .976 |

EXAMPLE II

6-[3-(4-Biphenylylcarbonyl)propionamido]penicillanic acid.

The title compound is prepared by the procedure described in Example I, except that 6-aminopenicillanic acid is substituted for the 7-aminocephalosporanic acid.

Elemental Analysis for $C_{24}H_{24}N_2O_5S\cdot\frac{1}{2}H_2O$: Calc'd: C, 62.46; H, 5.46; N, 6.07. Found: C, 62-49; H, 5.74; N, 5.81.

| BA | SU |  | 6633 | 3.90 |
| HE | SP |  | 9955 | 31.3 |
| KL | PN |  | 10031 | 125 |
| NE | CA |  | 8193 | 3.90 |
| ST | AU |  | 6538P | .122 |
| ST | AU |  | SMITH | .122 |
| ST | AU |  | CHP | 7.81 |

EXAMPLE III

7-[3-(4-Biphenylylcarbonyl)propionamido]-3-methyl-8-oxo-5-thia-1-azabicyclo[4.2.0]oct-2-ene-2-carboxylic acid.

The title compound is prepared by the procedure described in Example I except that 7-aminodesacetoxycephalosporanic acid is substituted for 7-aminocephalosporanic acid.

Elemental Analysis for $C_{24}H_{22}N_2O_5S$: Calc'd: C, 63.71; H, 5.35; N, 6.19. Found C, 63.62; H, 5.04; N, 5.86.

| BA | SU |  | 6633 | 3.90 |
| ST | AU |  | 6538P | 1.95 |
| ST | AU |  | SMITH | 1.95 |
| ST | AU |  | CHP | 3.90 |
| ST | AU |  | 53-180 | 3.90 |

EXAMPLE IV

6-[3-(4-Biphenylylcarbonyl)propionamido]penicillanic acid O-methyloxime.

3-(4-Biphenylylcarbonyl)propionic acid (22.2 grams, 0.05 mole) is dissolved in 300 milliliters of dimethoxyethane. To the above solution an aqueous solution of methoxyamine hydrochloride (4.18 grams, 0.05 mole) and sodium acetate (4.10 grams, 0.05 mole) in 100 milliliter $H_2O$ is added. The mixture is heated to reflux for 18 hours. After a small amount of insoluble material is filtered off the solvent is removed under reduced pressure. The residual solid is dissolved in chloroform. The chloroform solution is washed with water and then dried over anhydrous magnesium sulfate. After the solvent is removed the crude material weighs 12.4 grams. The crude material is recrystallized from benzene. The recrystallized 3-(4-biphenylylcarbonyl)propionic acid o-methyl-oxamic melts at 152°–4°C.

Elemental Analysis for $C_{17}H_{17}NO_3$: Calc'd: C, 72.06; H, 6.05; N, 4.94. Found: C, 72.72; H, 6.12; N, 4.03.

The title compound is prepared by the procedure described in Example 1, except that 3-(4-biphenylylcarbonyl)propionic acid O-methyloxime and 6-aminopenicillanic acid are used.

Elemental Analysis for $C_{25}H_{27}N_3O_5S$: Calc'd: C, 62.36; H, 5.65; N, 8.73. Found: C, 61.95; H, 5.88; N, 8.20.

| BA | SU |  | 6633 | 15.6 |
| HE | SP |  | 9955 | 125 |
| NE | CA |  | 8193 | 7.81 |
| ST | AU |  | 6538P | .244 |
| ST | AU |  | SMITH | .244 |
| ST | AU |  | CHP | 62.5 |

EXAMPLE V

7-[3-(4-Biphenylylcarbonyl)propionamido]cephalosporanic acid O-methyloxime.

The title compound is prepared by the procedure described in Example I except that 3-(4-biphenylylcarbonyl)propionic acid O-methyloxime, as produced in the preceding Example, is used.

Elemental Analysis for $C_{27}H_{27}N_3O_7S$: Calc'd: C, 60.32; H, 5.06; N, 7.82. Found: C, 60.58; H, 5.26; N, 7.40.

| BA | SU |  | 6633 | .488 |
| KL | PN |  | 10031 | 250 |
| NE | CA |  | 8193 | 31.3 |
| ST | AU |  | 6538P | .488 |
| ST | AU |  | SMITH | .488 |
| ST | AU |  | CHP | .976 |
| ST | AU |  | 53-180 | 1.95 |

What we claim is
1. A compound of the formula
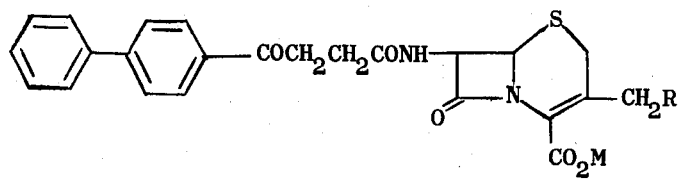
in which
R is hydrogen or alkanoyloxy of 2 to 6 carbon atoms, and
M is hydrogen, an alkali metal or the ammonium cation.
2. The compound of claim 1 which is 7-[3-(4-biphenylylcarbonyl)propionamido]cephalosporanic acid.
3. The compound of claim 1 which is 7-[3-(4-biphenylylcarbonyl)propionamido]-3-methyl-8-oxo-5-thia-1-azabicyclo[4.2.0]-oct-2-ene-2-carboxylic acid.
* * * * *